United States Patent
McNamara et al.

(10) Patent No.: US 7,837,985 B2
(45) Date of Patent: *Nov. 23, 2010

(54) POST APPLICATION EXPANDING COSMETIC COMPOSITION AND METHOD EMPLOYING SAME

(75) Inventors: William E. McNamara, Middletown, NY (US); Mark S. Garrison, Suffern, NY (US)

(73) Assignee: Avon Products, Inc, New York, NY (US)

( * ) Notice: Subject to any disclaimer, the term of this patent is extended or adjusted under 35 U.S.C. 154(b) by 1326 days.

This patent is subject to a terminal disclaimer.

(21) Appl. No.: 10/502,061

(22) PCT Filed: Dec. 19, 2003

(86) PCT No.: PCT/US03/40782

§ 371 (c)(1),
(2), (4) Date: Apr. 8, 2005

(87) PCT Pub. No.: WO2004/060334

PCT Pub. Date: Jul. 22, 2004

(65) Prior Publication Data

US 2005/0175563 A1    Aug. 11, 2005

Related U.S. Application Data

(63) Continuation-in-part of application No. 10/331,069, filed on Dec. 27, 2002.

(51) Int. Cl.
    *A61Q 1/10* (2006.01)
    *A61Q 5/00* (2006.01)
(52) U.S. Cl. ............ 424/70.7; 424/70.19; 424/70.21; 424/70.22
(58) Field of Classification Search .............. None
    See application file for complete search history.

(56) References Cited

U.S. PATENT DOCUMENTS

| | | |
|---|---|---|
| 3,541,581 A | 11/1970 | Monson |
| 3,876,771 A | 4/1975 | Denner |
| 4,528,111 A | 7/1985 | Su |
| 4,559,057 A * | 12/1985 | Bogaty et al. ............. 8/405 |
| 5,389,363 A * | 2/1995 | Snyder et al. ............. 424/70.7 |
| 5,800,825 A | 9/1998 | McMullen |
| 6,027,738 A | 2/2000 | Stepniewski et al. |
| 6,030,630 A | 2/2000 | Fleury et al. |
| 6,096,702 A | 8/2000 | Ramirez et al. |
| 6,177,092 B1 | 1/2001 | Lentini et al. |
| 6,224,851 B1 | 5/2001 | Bara |
| 6,251,375 B1 | 6/2001 | Bara |
| 6,328,950 B1 | 12/2001 | Franzke et al. |
| 6,440,923 B1 | 8/2002 | Lyle et al. |
| 2002/0122772 A1 * | 9/2002 | Lukenbach et al. ........... 424/44 |

FOREIGN PATENT DOCUMENTS

| | | |
|---|---|---|
| JP | 03-31389 A | 2/1991 |
| JP | 03-178923 A | 8/1991 |
| JP | 07-53325 A | 2/1995 |
| JP | 08-73839 A | 3/1996 |
| JP | 52-5683 A | 1/1997 |
| JP | 09-77629 A | 3/1997 |
| JP | 2003-201217 A | 7/2003 |
| WO | 03/043598 A1 | 5/2003 |

OTHER PUBLICATIONS

Database WPI Week 199722 Thomson Scientific, London, GB: AN 1997-241614; AP002515877 & JP 09077629 A (Mandom KK) Mar. 25, 1997 *abstract*.
U.S. Appl. No. 10/331,069, filed Dec. 27, 2002, W. McNamara et al.
U.S. Appl. No. 10/532,361, filed Apr. 20, 2005, W. McNamara et al.
U.S. Appl. No. 10/532,362, filed Apr. 20, 2005, W. McNamara et al.

* cited by examiner

*Primary Examiner*—Jyothsna A Venkat
(74) *Attorney, Agent, or Firm*—Charles J. Zeller; Juan M. McGillyevddy; Anthony M. Santini

(57) ABSTRACT

The present invention provides a post-application expanding composition for application to keratin fibers, preferably hair, more preferably the hair of the scalp, eyebrows and eyelashes, and most preferably the eyelashes. The composition comprises one or more surfactants, a solvent for the surfactant(s), a volatile agent, a film forming agent and, optionally, a colorant, preferably a pigment. The present invention also provides a method for imparting a volumizing effect to hair of the scalp, eyebrows or eyelashes by applying thereto the post-expanding composition of the invention.

29 Claims, No Drawings

POST APPLICATION EXPANDING COSMETIC COMPOSITION AND METHOD EMPLOYING SAME

This application is a continuation-in-part of application Ser. No. 10/331,069, filed Dec. 27, 2002.

BACKGROUND OF THE INVENTION

1. Field of the Invention

The present invention provides a post-application expanding composition for application to keratin fibers, preferably hair, more preferably the hair of the scalp, eyebrows and eyelashes, and most preferably the eyelashes. The composition comprises an agent which due to its volatility, will expand after it is applied to hair ("a volatile agent"), a film forming agent and, optionally, a colorant, preferably a pigment. The present invention also provides a method for imparting a volumizing effect to hair of the scalp, eyebrows or eyelashes by applying thereto a post-application expanding composition in accordance with the invention.

2. Description of the Related Art

Prior to the present invention, personal care preparations for the volumizing of hair, in particular eye lashes, employed the use of mascara in a building fashion. That is, several coats had to be applied to gain the desired volume or expansion effect. Depending on the type of mascara product and consumer preferences, the amount of manipulation required could be quite extensive. This is evident in the large number of brush strokes needed to arrive at a clump-free yet volumized look. Currently, it has been observed that women use an average of approximately 10 to 12 brush strokes to apply mascara to one pair of eyelashes. Depending upon the user and desired level of volume, this number of brush strokes can be multiplied by 2 to 4 times. Women desire a mascara composition that can achieve the appearance of thicker eyelashes with a lower number of brush strokes, i.e., less manipulation, or even improved thickness with the same amount of brush strokes. Consumers, men and women alike, also desire products that will provide the appearance of thicker hair.

Post-application expanding compositions are known in the art. For example, U.S. Pat. No. 3,541,581 discloses a cleansing or cosmetic composition in the form of a stable, post-foaming shaving gel. The disclosed gel has a yield value sufficiently high to substantially restrain the composition from foaming for at least about 60 seconds under static ambient conditions. The '581 patentee states that an object of the invention is to provide a lather-producing composition that, in addition to possessing the desirable properties of prior art compositions, is characterized by being discharged as a stable gel that is substantially free from foaming. After it is spread over the skin and beard, the gel produces a post generating foam. The purpose of the invention is to provide a lather, in-situ, on the surface of the skin so as to facilitate shaving of facial hair. The invention is also disclosed to be useful in topical applications for cleansing. Moreover, coloring materials, such as dyes may be used if desired.

U.S. Pat. No. 4,405,489 discloses a process for continuously producing a post-foaming gel and for packaging same. The process comprises admixing separately metered amounts of an aqueous soap ingredient and a post-foaming agent to form an intimate mixture thereof. The mixture is passed to a filling machine for packaging the gel. The steps are affected in a continuous flow system under pressure. The mixture is maintained within the continuous flow system for a time and at a pressure and temperature sufficient to produce a post-foaming gel that is capable of continuously flowing through the system to the filling machine for packaging thereof.

U.S. Pat. No. 4,651,503 is also directed to a method for forming and packaging a delayed foaming gel. The disclosed invention forms an emulsion in the filling head and then forms the delayed foaming gel in the container after it is filled therein.

U.S. Pat. No. 4,528,111 discloses a stable shaving cream gel that is asserted to possess superior foaming and after-feel characteristics. Various compatible additives which do not adversely affect the gel structure may be added in minor amounts. Coloring materials are included among the materials exemplified as suitable for such purpose. A combination of the dyes D & C Yellow #10 and F D & C Blue #1 is employed in Examples 6 through 10. They are however used in very low concentration. For example 1.2% of a 1% trituration of D& C Yellow #10 dye and 0.45% of a 1% trituration of F D & C Blue #1 dye are employed in Example 7.

Though the post-foaming compositions of the prior art have been used for shaving facial hair and though such compositions may contain minor amounts of a dye to impart to the composition a coloration more pleasing to the consumer, such compositions have heretofore found no further use.

Prior art mascara products require a great deal of manipulation to gain the desired effect of volume. Some prior art products are high viscosity or paste like and are usually comprised of waxes, high pigment loads and volatile substances. Though such prior art products may contain volatiles, such as volatile silicones or petroleum distillates, the volatiles do not function as blowing agents to promote foam formation. Such types of mascaras are hard to manipulate and consequently require excess stroking on application to the eyelashes in order to prevent clumping. Other prior art products have a lower viscosity. They use film formers and require multiple applications to build up to a desired level of volume. With all prior art mascara products, the product experiences a loss of volume after application to the eyelashes. This is due to evaporation of solvents which causes the product to actually shrink down. The composition of the present invention eliminates these deficiencies of the prior art. The composition of the present invention requires much less manipulation upon application and actually surprisingly increases volume, in a substantially uniform manner, immediately after application to the eyelashes. The properties of the composition of the present invention make it easy to evenly apply same to the eyelashes thereby eliminating clumping.

The present inventor has discovered that compositions that expand after application, such as the delayed post-foaming compositions of the prior art, can be surprisingly and advantageously modified and employed to improve the aesthetic appearance of keratin fibers, especially hair of the scalp, eyebrows or eyelashes.

SUMMARY OF THE INVENTION

The present invention relates to a composition for application to keratin fibers, such as hair fibers of the scalp, eyebrows and eyelashes. More particularly, the invention relates to a composition that expands after application, such as a post-foaming composition, and to a method of using such composition to impart volume and/or color to keratin fibers of the scalp, eyebrows and eyelashes.

The present invention provides a composition that contains a surfactant, a solvent for the surfactant, a film former and a volatile agent that will expand after the composition is applied to keratin fibers of the scalp, eyebrows and eyelashes.

The film-forming agent is present in an amount effective to form a film after the composition is applied to a keratin fiber. Alternatively, a colorant (preferably, a pigment) is present in an amount sufficient to mask the color of the foam formed after the composition is applied to a keratin fiber. Preferably, both the film-forming agent and the colorant are present. Most preferably, the colorant is present in an amount effective to impart a color to the keratin fibers onto which the composition is applied.

In its broadest form, the present invention includes any cosmetically acceptable composition for application to keratin fibers of the scalp, eyebrows and/or eyelashes wherein the composition expands when applied to such fibers, upon application or after a predetermined time period thereafter, then sets up in its expanded state, to provide beneficial characteristics to the fibers, such as a volumizing effect.

DETAILED DESCRIPTION OF THE INVENTION

The composition of the present invention is comprised of (i) a post-foaming component comprising a volatile agent, one or more surfactants, and a solvent for the surfactant(s) and (ii) a film forming agent or colorant. Preferably, the composition is comprised of (i) a post-foaming component comprising a volatile agent and one or more surfactants and (ii) a film forming agent. More preferably, the composition is comprised of (i) a post-foaming component comprising a volatile agent, one or more surfactants, and a solvent for the surfactant(s), (ii) a film forming agent and (iii) a colorant, preferably, a pigment.

Post-Foaming Component

The first necessary component of the post-application expanding composition of the present invention is a post-foaming component comprised of one or more surfactants, a solvent for the surfactant(s), and a volatile agent (blowing agent) that foams the surfactant(s).

Post-foaming compositions, particularly post-foaming gel compositions, are known in the art. For purposes of the present invention, a post-foaming composition is a composition that does not create a foam as it is dispensed from its container, but creates a foam after exposure to atmospheric pressure for at least 2 seconds. However, a post-foaming composition may foam even sooner when exposed to mechanical manipulation and/or to temperatures greater than ambient temperature. Such post-foaming compositions are also within the scope of the present invention.

It should be noted that as used herein, the terms "post-expanding" and "post-application expanding" are synonymous.

It should be appreciated that any cosmetically acceptable post-foaming system can be employed in preparing the post-application expanding compositions of the present invention. The post-foaming gels of U.S. Pat. Nos. 2,995,521; 3,541,581; 3,654,167; 4,405,489; 4,528,111; 4,651,503; 6,165,456 and US Patent Application Publication U.S. 2002/0122772 A1, the entire disclosures of which are incorporated herein by reference, are non-limiting examples of suitable post-foaming gels. The post-foaming gels of U.S. Pat. Nos. 3,541,581; 4,528,111 and US Patent Application Publication US 202/0122772 A1 are preferred. The post-foaming gel of U.S. Pat. No. 3,541,581 is most preferred as the post-foaming component of the post-expanding composition of the present invention. For ease of removal of the composition, using a water-rinseable post-foaming component is preferred.

When the composition of the present invention is based upon the system described in U.S. Pat. No. 3,541,581, in other words, when the composition of the present invention utilizes the post-foaming gel of the '581 patent as the post-foaming component of the composition of the present invention, the composition of the present invention is in the form of a stable, post-foaming gel comprised of (i) about 30 to about 90% by weight water; (ii) a surfactant selected from a group consisting of anionic surfactants, nonionic surfactants, amphoteric surfactants, (including zwitterionic surfactant) and mixtures thereof, with the proviso that when a water-soluble salt of a fatty acid is employed as the surfactant, it is present in an amount of about 0.1 to about 25% by weight and when the surfactant employed is other than a water-soluble salt of a fatty acid, it is present in an amount of about 0.1 to about 12.0% by weight; (iii) about 0.1 to about 15% by weight of volatile liquid post-foaming material ("a volatile agent") selected from the group consisting of aliphatic hydrocarbons, halogenated hydrocarbons, perhalogenated hydrocarbons (particularly perfluorinated hydrocarbons), and mixtures thereof; (iv) about 0.1 to about 0.8% by weight of an antimicrobial or preservative; (v) about 1 to about 30% by weight of a polymer film forming agent (as will be elaborated upon more fully later on in the present disclosure); (vi) about 0.5 to about 15% by weight of pigment (including coated and uncoated pigments and combinations thereof); and (vii) about 0.01 to about 5% by weight of at least one water-soluble gelling agent which when incorporated in the composition provides a gel having a yield value high enough to restrain the composition from foaming for at least 2, preferably 5, and more preferably 10 seconds, under static ambient conditions and/or in combination with mechanical manipulation, e.g., with a mascara applicator. A composition of the present invention based upon the post-foaming gel of U.S. Pat. No. 3,541,581 is further described in Example 1 of the present application.

Although the focus has been on the use of a post-foaming component (surfactant(s), solvent and volatile agent) in accordance with U.S. Pat. No. 3,541,581, as noted earlier, any topically acceptable post-foaming system can be employed as the post-foaming component of the composition of the present invention. For example, the post-foaming gel composition of U.S. Pat. No. 4,528,111 or the self-foaming gel of US Patent Application Publication U.S. 2002/0122772 A1 may be employed as the post-foaming component of the composition of the present invention.

The post-foaming gel of U.S. Pat. No. 4,528,111 is also suitable as the post-foaming component of the composition of the present invention. The post-foaming system of the '111 patent is provided by the interpolymer gel reaction products of selective anionic polymers, and selective cationic polymers. This gel is a water soluble interpolymer gel reaction product formed by the rapid and intensive interaction of two oppositely charged selective polymers; a quaternized cationic polymer bearing positive charges and selected from the group consisting of poly(diallyldimethylchloride-co-acrylamide) and a quaternary ammonium cellulose ether polymer, and an anionic polymer bearing negative charges and selected from the group consisting of poly(2-acrylamido-2-methylpropane sulfonic acid) and alginic acid. The selective group of anionic polymers include: polysulfonic acid ("PSA") such as poly(2-acrylamido-2-methylpropane sulfonic acid) available as POLYMER HSP 1180 from Henkel as a 15% aqueous solution and alginic acid in free acid form, which is water-insoluble and available as a powder. Typically, what is employed is about 0.05-5%, preferably 0.1-1.0%, of a water-soluble interpolymer gel reaction product of a quaternized cationic polymer selected from the group consisting of poly (diallyldimethyl chloride-co-acrylamide) and a quaternary ammonium cellulose ether polymer, and an anionic polymer selected from the group consisting of poly(2-acrylamido-2-methylpropane sulfonic acid) and alginic acid; and about 55-94% water.

The method of preparing interpolymer gels that can be employed for purposes of the present invention comprises the rapid mixing, at a rate of at least 1000 rpm, of high concentrations of the aforesaid selective anionic and selective cationic polymers in an aqueous medium substantially free of interfering ingredients, such as salt, amphoteric, anionic and cationic compounds. The selective group of quaternized cationic polymers used in the preparation of the water-soluble interpolymer gels are water-soluble and include poly(diallyldimethylammonium chloride-co-acrylamide), which is the copolymer of dimethyldiallylammonium chloride and of acrylamide, having a molecular weight of more than 500,000, and sold under the name MERQUAT 550 and MERQUAT S by the Merck Company and obtainable as an 8% aqueous solution.

The interpolymer reactions of polycationic and polyanionic materials produce reaction products ranging from insoluble precipitates to water-soluble and water-insoluble but swellable gels. The reaction product of poly(2-acrylamido-2-methylpropane sulfonic acid) (PSA) and MERQUAT 550 loses its fluidity and forms a clear gel at 7.5% PSA and 4% MERQUAT 550, while the individual solutions flow freely. The minimum concentration required for the formation of the interpolymer gel reaction product of PSA and MERQUAT 550 is 7.5% PSA and 4% MERQUAT 550. The aqueous reaction mixture, which is the sum total of both solutions, contains 3.75% PSA and 2% MERQUAT 550. The gel, when diluted to 1.89% PSA and 0.96% MERQUAT 550, still exhibits a high viscosity of more than 24,000 cps, while the individual solutions show a viscosity of 400 cps and 200 cps, respectively. This gel is prepared by vigorously mixing a 7.5-15% solution of PSA and a 4-8% solution of MERQUAT 550. Slow mixing results in white precipitates within the gel. Further dilution of the two solutions before mixing also results in white precipitates when they are mixed. This clearly indicates that it requires fast and intensive interactions of the two opposite charges to ensure obtaining the maximum amount of ion pair formation to give the gel structure. Whether the gel is water-soluble or water-insoluble depends on the formation of intimate or loose ion pairs which, in turn, depends on the charge density and structure of the polyelectrolytes.

Surfactant System

As noted earlier herein, the post-foaming gel of US Patent Application Publication U.S. 2002/0122772 A1 can be employed as the post-foaming component of the composition of the present invention.

The post-foaming component employed in the post-application expanding composition of the present invention includes a surfactant system comprised of one or more surfactants and a solvent for the surfactant(s), preferably, water or a mixture of water and one or more alcohols, most preferably water. The surfactant can be an anionic surfactant, an amphoteric or zwitterionic surfactant, a nonionic surfactant or a mixture thereof.

Preferably, the anionic surfactant is selected from the group consisting of water-soluble salts of fatty acids, preferably $C_{10}$ to $C_{22}$ fatty acids, alkyl sulfates; alkyl ether sulfates; alkyl monoglyceryl ether sulfates; alkyl monoglyceride sulfates; alkyl monoglyceride sulfonates; alkyl sulfonates; alkylaryl sulfonates; alkyl sulfosuccinates; alkyl ether sulfosuccinates; alkyl sulfosuccinates; alkyl amidosulfosuccinates; alkyl carboxylates; alkyl amidoethercarboxylates; alkyl succinates; fatty acyl sarcosinates; fatty acyl amino acids; fatty acyl taurates; fatty alkyl sulfoacetates; alkyl phosphates; alkyl ether phosphates; and mixtures thereof. A preferred anionic surfactant is sodium laureth sulfate.

Examples of amphoteric and zwitterionic surfactants that can be employed include amphocarboxylates, alkyl betaines, amidoalkyl betaines, amidoalkyl sultaines, amphophosphates, phosphobetaines, pyrophosphobetaines, carboxyalkyl alkyl polyamines, alkyl amino monoacetates, alkyl amino diacetates, and mixtures thereof. Betaine surfactants are preferred. Cocamidopropyl betaine is most preferred.

One class of nonionic surfactants useful in the present invention are polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, alpha-methyl glucoside, polyglucose having an average of about 1 to about 3 glucose residues per molecule, glycerin, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester.

Examples of preferred polyoxyethylene derivatives of polyol esters include PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del. under the tradename, "ATLAS G4280." Polysorbate 20, which is the laurate monoester of a mixture of sorbitol and sorbitol anhydrides condensed with approximately 20 moles of ethylene oxide, is available commercially from Uniqema Company under the trade name "TWEEN 20."

Another class of suitable nonionic surfactants includes long chain alkyl glucosides or polyglucosides, which are the condensation products of (a) a long chain alcohol containing from about 6 to about 22 carbon atoms, preferably from about 8 to about 14 carbon atoms, with (b) glucose or a glucose-containing polymer. The alkyl glucosides have about 1 to about 6 glucose residues per molecule of alkyl glucoside. Alkyl glucosides are the preferred nonionic surfactants. Suitable alkyl glucosides include, but are not limited to, octyl glucoside, decyl glucoside, and lauryl glucoside.

Additional nonionic surfactants that may be used include: ethylene oxide/propylene oxide copolymers, (poly)glycerol esters and fatty acids, fatty acid alkanolamides, alkoxylated mono and di-alcanolamides, aminoxides, ethoxylated fatty alcohols and esters, fatty acid sucrose esters, ethoxylated glucosides, and fatty gluconamides.

Volatile Agent

In addition to the surfactant system, the post-foaming component includes a volatile or blowing agent to initiate post foaming. Suitable for this purpose are volatile or blowing agent(s) (halogenated or non-halogenated, synthetic or naturally occurring) with a vapor pressure from about 0.5 Torr to about 30,000 Torr, preferably from about 5.0 Torr to about 5,000 Torr, and more preferably, from about 100 Torr to about 2,500 Torr, at a temperature of about 0° to about 100° C.

Examples of preferred volatile agents include but are not limited to n-pentane, isopentane, neopentane, n-butane, isobutane, isobutene, cyclopentane, hexane, trichlorotrifluorethane, 1,2-dichloro,1,1,2,2-tetrafluoroethane, hydrofluoroethers (eg. methyl perfluorobutuyl ether/methyl perfluoroisobutyl ether (CF-61, NOVEC-7100, a product of 3M), ethyl perfluorobutyl ether/ethyl perfluoroisobutyl ether (CF-76, NOVEC HFE-7200, a product of 3M), 2-trifluoromethyl-3-ethoxydodecafluorohexane (NOVEC HFE-7500, a product of 3M)), methyl perfluoropropyl ether, and mixtures thereof. Other suitable volatile agents may include, but are not limited to, perfluoromethylcyclohexane, manufactured by F2 Chemicals Ltd. under the trade name Flutec PP2, or Flutec PC2; perfluoromethylcyclopentane, available from the same company under the trade name Flutec PC1C; and perfluorohexane and perfluorodimethylcyclohexane, available from the same company under the trade names Flutec PC1 and Flutec PC3, respectively. Perfluorodimethylcyclopentane (molecular weight of about 350) is also expected to be suitable in the present invention.

Film Forming Agent

The post-application expanding composition of the present invention preferably contains a film forming agent.

The film forming agent is present in an amount sufficient so that when the post-application expanding composition is applied to the hair of the scalp, eyebrows or eyelashes, and the post-foaming component begins to foam, the film formed by the film forming agent will stabilize at least a portion of the foam (as will be elaborated on more fully below) thereby imparting a volumizing effect to the hair fibers upon which the composition of the invention is applied.

The film forming agent can be natural or synthetic. Film forming waxes are known in the art and can be employed alone or in combination with one or more natural or synthetic film forming agents. Synthetic film forming agents, for example, acrylates copolymers and/or methacrylates copolymers, acrylamide copolymers, and mixtures thereof, are particularly preferred.

Water-soluble film forming agents that can be utilized are exemplified in monographs 27-33 of the International Cosmetic Ingredient Dictionary and Handbook, $9^{th}$ Ed. (2002). Particularly preferred film formers include; (i) acrylamide copolymer; for example, acrylamides/DMAPA acrylates/methoxy PEG methacrylate copolymer, acrylamide/sodium acrylate copolymer, acrylamide/sodium acryloyldimethyltaurate copolymer, acrylates/acrylamide copolymer, acrylates/t-butylacrylamide copolymers and (ii) acrylates copolymer, for example, BF Goodrich's AVALURE AC115, AVALURE AC118, AVALURE AC120, AVALURE AC125, AVALURE AC210 and AVALURE AC315; LCW's COVACRYL A15 and COVACRYL E14; Daito Kasei's DAITOSOL 5000 AD; acrylates/C1-2 succinates/hydroxyacrylates copolymer; acrylates/dimethicone copolymer; acrylates/dimethicone methacrylate/ethylhexyl acrylate copolymer; acrylates/dimethylaminoethyl methacrylate copolymer; acrylates/ethylhexyl acrylate copolymer; acrylates/ethylhexylacrylate/HEMA/styrene copolymer; acrylates/hydroxyesters acrylates copolymer; acrylates/laurylacrylate/stearyl acrylate/ethylamine oxide methacrylate copolymer; acrylates/octylacrylamide copolymer; acrylates/propyl trimethicone methacrylate copolymer; acrylates/stearyl acrylate/dimethicone methacrylate copolymer; acrylates/VP copolymer; and acrylates/VP/dimethylaminoethyl methacrylate/diacetone acrylamide/hydroxypropyl acrylate copolymer. Polyvinyl alcohol and water-soluble polyvinyl esters can also be employed.

More preferred film-forming agents useful in the present invention include sodium acrylates copolymer, sodium acryloldimethyl taurate copolymer, ethyl methacrylate/N-butyl acrylate/2-methylhexyl acrylate copolymer, and butyl acrylate/hydroxyethyl methacrylate copolymer. Polymeric blends, such as Interpolymer's SYNTRAN EX-100 and Kobo Product's DAITOSOL 5000 SJ are also useful as synthetic polymer film forming agent in the composition of the present invention.

Depending on whether the post-application expanding composition of the present invention is mostly water or mostly oil, an appropriate film forming agent can be utilized. In point of fact, when the post-expanding composition is an emulsion, a water-soluble film forming agent, an oil-soluble film forming agent or a water-soluble film forming agent and an oil-soluble film forming agent can be employed.

When the post-expanding composition is mostly oil (either organic or synthetic), an oil-soluble synthetic polymer can employed as the film forming agent. Suitable oil-soluble synthetic polymers include, for example, polyurethane-1, polyurethane-2, polyurethane-3, polyurethane-4, polyurethane-5, polyurethane-6, polyurethane-7, polyurethane-8, polyurethane-9, polyurethane-10, polyurethane-1, polyethylene, oxidized polyethylene, polypropylene, tetramethyl tetraphenyl trisiloxane, tricontanyl trimethyl pentaphenyl trisiloxane, styrene/MA copolymer, styrene/DVB copolymer, various quaternary ammonium synthetic polymers, and crosspolymer, such as PVM/MA decadiene crosspolymer.

Various oil-soluble derivatives of polyvinyl pyrrolidone copolymers can also be used, with polyvinylpyrrolidone/decene copolymer and poly (vinyl pyrrolidone/1-triacontene) being preferred. The ethyl ester of PVM/MA copolymer can be used as well.

Water-soluble polyurethanes can also be used as the film forming agent, for example, EPQ 30 and EPQ 31 (Johnson Polymers) and the polyester urethane GK 910 (ALZO International, Inc.).

Preferably, the film forming agent is present in the post-application expanding composition of the invention in a concentration of from about 1 to about 50% by weight, more preferably about 5 to about 40% by weight, most preferably about 8 to about 30% by weight, and optimally about 10 to about 25% by weight, based on the total weight of the post-application expanding composition.

When the post-expanding composition of the present invention is applied on hair fibers, such as eyelashes, the volatile agent will release and cause the surfactant and solvent for the surfactant to swell/expand the composition. When the film forming agent sets, it fixes at least a portion of the swelled/expanded composition on the eyelashes in its swelled/expanded state, thereby imparting a volumizing effect to the eyelashes.

As will be discussed below, the composition of the present invention may contain a pigment dispersion that includes one or more film forming agents. The amount of film forming agent contributed by the pigment dispersion is considered in the total amount of film forming agent in the post-application expanding composition. For example, if the post-application expanding composition contains 50 wt %, based on the total weight of the composition, of a pigment dispersion that further contains 40 wt %, based on the total weight of the pigment dispersion, of a film forming agent, the composition of the invention has 20 wt %, based on the total weight of the composition, film forming agent (due to the contribution of the pigment dispersion). Additional film forming agent may be added. However, from a cost standpoint it is preferred that the total not exceed about 50 wt %, based upon the total weight of the composition.

While the present inventor does not wish to be bound to any one theory, it is believed that during the post-foaming action the film forming agent will set, thus, locking or sealing the foam lattice in place, either by forming a film, preferably a flexible film, over at least a portion of the surface of the foam or by increasing the rigidity of the foam lattice thereby stabilizing the foam. Preferably, a film will form over greater than about 50 percent of the surface of the foam, and more preferably over greater than about 75 percent of the surface of the foam. Alternatively, the film forming agent increases the rigidity of the foam lattice by greater than about 50%, and more preferably by greater than about 75%.

It is preferred that the composition of the present invention be left on the hair fibers for a predetermined period of time; in particular, at least 2 hours, more preferably, 2 to 12 hours.

Since the compositions of the present invention are preferably used as cosmetic compositions for application to the hair, eyebrow and eyelashes, it is preferred that the film forming agent is of the type and amount to allow the composition to be removed from the hair fiber with water, mild soap or a mild cosmetic cleanser. Where water washability/rinseability is not required, a non-water-soluble film forming agent can of course be employed.

Colorant

An optional component of the post-application expanding composition of the present invention is a colorant, preferably a pigment.

The novel cosmetic composition of the present invention can be transparent or colored. Preferably, when it is to be applied to the eyelashes, it is colored. Prior art post-foaming gels have included colorants as an optional ingredient to give the composition a pleasing appearance. The composition of the present invention, optionally, incorporates one or more colorants in an amount sufficient to mask the color of the foam, which is usually white, so that when the composition of the present invention is applied to the hair, it imparts a color thereto other than white. Naturally, with white hair, a colorant need not be employed. When the composition of the present invention contains, for example pigment in an amount sufficient to mask the color of the foam and impart a color to keratin fibers treated with the composition, the composition of the invention can be used as a mascara, a hair-volumizing dye or colorant or an eyebrow composition, among others.

Virtually any level of colorant, preferably pigment, can be used so long as it substantially alters (preferably masks) the color of the foam that is otherwise produced on the hair absent the colorant. Preferably the colorant, preferably pigment(s), is present in an amount sufficient to impart a color to the hair fiber on which it is applied. The post-application expanding composition of the invention generally includes about 0.5 to about 30% by weight, preferably about 1 to 15% by weight, and more preferably about 2 to about 10% by weight, colorant, preferably pigment, based upon the total weight of the post-application expanding composition.

Thus, the post-application expanding composition of the present invention preferably includes, as a component, a colorant, preferably a pigment, most preferably a pigment dispersion containing one or more film forming agents, which are preferably film forming polymers. The pigment dispersion is preferred because of the physical attributes associated with a finely dispersed, clump free, color solution providing added film forming capability. A material that is particularly preferred, since it performs extremely well, is the material WSJ24BAMP available from Kobo Products. This material is comprised of water (43 to 50%, by weight); ethylmethacrylate/N-butylacrylate/2-methylhexyl acrylate copolymer (25 to 30%, by weight); iron II, III oxide (22 to 26% by weight); sodium acryloldimethyl taurate copolymer (0.1 to 5%, by weight); 2-amino-2-methyl-1-propanol (0.1 to 5%, by weight); and, optionally, a preservative blend (0.1 to 1%, by weight). Powdered pigments (Iron II, III oxide) may also be utilized and, when combined with the proper water-soluble polymeric film forming agents and properly dispersed, can accomplish the desired effect. WSJ24BAMP, the preferred material, is generally employed in an amount of from about 5 to about 50% by weight, based on the total weight of the post-application expanding composition. It should be appreciated that in lieu of the about 0.5 to about 30% by weight of pigment, the post-application expanding composition can contain from about 0.5 to about 90% by weight of a pigment dispersion comprised of polymeric film forming agents, pigment, emulsifier and other adjuvants.

Optional Ingredients

The post-application expanding composition of the present invention can optionally contain ingredients typically employed in cosmetics, provided they do not adversely affect the performance of the composition so as to prevent realization of its beneficial effects. Such additional ingredients include, for example, vitamins, antioxidants, preservatives, dyeing agents, fixative agents, styling agents and conditioning agents.

Cosmetic Composition

The present invention provides a self-foaming composition, which when applied foams or swells to a specified volume. One application merely requires perhaps 2 to 6 brush strokes in order to achieve the desired volume. Most desirably, the composition is applied to the eyelashes and the composition contains a sufficient amount of a pigment to mask the natural color of the foam and impart color so that the resultant composition can be employed as a mascara which, due to its volumizing effect, imparts a thickened appearance to the eyelashes upon which the composition is applied.

It should be appreciated that the composition of the present invention can be formulated as a gel, cream, emulsion, low or high viscosity liquid or semi-solid.

The composition of the present invention can be packaged in a pressurized system or, when long term storage stability is not required, in a non-pressurized system. When pressurized, it will be suitably packaged in an aerosol container.

The following examples are offered merely to further illustrate the present invention, they are not intended to be limiting in any respect. It should be appreciated that unless otherwise indicated all percentages utilized herein are percent by weight, based on the total weight of the post-application expanding composition.

Examples 1 through 12, which follow, illustrate post-application expanding compositions that employ a blowing agent to generate the post-foaming action and require packaging in a pressurized container.

A general formula for a particularly preferred mascara formulation in accordance with the present invention is set forth in the following Example 1.

EXAMPLE 1

When the cosmetic composition of the present invention employs a post-foaming component as described in U.S. Pat. No. 3,541,581, the post-application expanding composition may include:

1. A solvent or solublizing component that provides lathering properties, is compatible with film forming agents and allows for the manufacture of a stable gel. Water, deionized, distilled or even tap water, is preferred as the solublizing component. It is generally employed in a range of about 30 to about 90% by weight, based on the total weight of the composition. It should be appreciated that when the composition is to be employed on the hair of the scalp, the solubilizing component can be an alcohol or mixture of one or more alcohols and water.
2. A water-soluble soap component prepared by alkaline hydrolysis of a $C_{10}$-$C_{22}$ fatty acid, for example, through use of ammonia, low molecular weight amines, especially alkanolamines and alkali metals, especially sodium and potassium. Preferably the water-soluble component is selected from sodium, potassium and triethanolamine salts of high molecular weight fatty acids ($C_{10}$-$C_{22}$). Palmitic acid, stearic acid, oleic acid, myristic acid, palm and coconut oil fatty acids are preferred. Additionally, betaines and sultaines can be employed, alone or in combination with the previously mentioned sodium, potassium or triethanolamine salts of fatty acids, so as to accomplish the foaming action, or simply for boosting foaming. Typically, the water-soluble soap component is present in a concentration of from about 0.1 to about 25% by weight, based on the total weight of the composition.
3. A water-soluble viscosity increasing or gelling component selected from synthetic sucrose derivatives (such as carbomer), cellulose gums (such as hydroxyethyl cellulose and carboxymethyl cellulose) and natural hydrophilic colloids (such as carrageenans). The water-soluble viscosity increasing or gelling agent is generally employed in a concentration of from about 0.1 to about 5% by weight, based on the total weight of the composition, depending upon the choice of thickener.
4. A film forming agent in a concentration of from about 1 to about 50% by weight, based on the total weight of the composition.
5. A volatile or blowing agent to initiate post-foaming.
6. A colorant is optionally included in an amount from about 1 to about 70% by weight, based on the total weight of the composition. The colorant is preferably a pigment, and most preferably a pigment dispersion.
7. A preservative is optionally included. NIPASTAT, GERMABEN II, LIQUAPAR OIL, AND LIQUAPAR PE are examples of preservative systems that can be utilized. They are generally employed in a concentration effective to inhibit microbial growth. Preferably, the preservative is present in an amount about 0.1 to about 0.8% by weight, based on the total weight of the composition.

EXAMPLE 2

Mascara Formulation

| Ingredient | wt. % |
|---|---|
| Distilled water | QS |
| Surfactant or mixtures of surfactants* | 0.1-20 |
| Volatile agent or mixture of volatile agents | 0.1-15 |
| Gelling agent | 0.01-5 |
| WSJ24BAMP (pigment/film forming agent/water mix) | 5-50 |
| SYNTRAN EX-100 (acrylates copolymer/water/surfactant) | 1-30 |
| Antimicrobial | 0.1-0.8 |

*It should be noted that when the surfactant is a water-soluble salt of a fatty acid, it is preferably employed in a concentration of about 0.1 to 20% and when it is an anionic surfactant other than a water-soluble salt of a fatty acid, or a nonionic surfactant, or amphoteric or zwitterionic surfactant or mixture thereof, it is preferably employed in a concentration of about 0.1 to 12%.

EXAMPLE 3-9

Mascara Formulations

| Ingredient | 3 wt. % | 4 wt. % | 5 wt. % | 6 wt. % | 7 wt. % | 8 wt. % | 9 wt. % |
|---|---|---|---|---|---|---|---|
| Palmitic acid | 5.0 | 4.0 | — | 4.0 | 3.0 | 4.0 | 4.0 |
| Triethanolamine 99% | 3.0 | 1.0 | — | 1.5 | 1.5 | 2.0 | 1.0 |
| WSJ24BAMP (Kobo products) | 29.35 | 25.0 | 25.0 | 25.0 | 25.0 | 25.0 | 25.0 |
| SYNTRAN EX-100 Interpolymer) | 18.0 | 18.0 | 18.0 | 10.0 | 18.0 | 16.5 | 18.0 |
| AGAR 150C (TIC Gums) | 0.25 | — | — | — | — | — | — |
| Polyglycerol diisostearate | 0.45 | — | — | — | — | — | — |
| Sodium laureth ether sulfate | — | — | 0.7 | — | — | — | — |
| Cocamidopropyl betaine | 0.1 | 0.5 | 3.0 | — | — | — | 0.5 |
| GERMABEN II | 0.2 | — | — | 0.5 | — | — | — |
| SALCARE AST (Ciba Specialty Chemical) | 0.2 | — | — | — | — | — | — |
| Isopentane | 2.4 | 1.5 | 1.5 | — | 1.5 | 1.5 | 1.5 |
| Butane/pentane (25/75) | — | — | — | 2.0 | — | — | — |
| DAITOSOL 5000 SJ | — | 12.0 | 10.0 | 5.0 | 12.0 | 12.0 | 12.0 |
| Hydroxyethyl cellulose | — | 0.5 | 1.0 | — | 0.5 | 0.5 | 0.5 |
| Oleth-3 phosphate | — | 0.5 | — | — | 0.5 | 0.5 | 0.5 |
| Isoceteth-20 | 0.45 | 0.5 | — | 1.0 | 0.5 | 0.5 | 0.5 |
| LIQUAPAR | — | 0.5 | 0.5 | — | 0.5 | 0.5 | 0.5 |
| PEG-150 Distearate | — | — | — | 1.7 | — | — | — |
| MERQUAT S POLYMER (8% solution | — | — | — | 0.1 | — | — | — |
| PSA polymer (15% solution) | — | — | — | 0.1 | — | — | — |
| Myristic acid | — | — | — | — | 1.0 | — | — |
| Stearic acid | — | — | — | — | 1.0 | 1.0 | — |
| Deionized water QS to | 100 | 100 | 100 | 100 | 100 | 100 | 100 |

For use as a volumizer for hair other than eyelashes a particularly preferred general formulation is set forth in the following Example 10.

EXAMPLE 10

Volumizing Product for Hair (Other than Eyelashes)

| Ingredient | wt. % |
| --- | --- |
| Water-soluble soap, foam booster or combination thereof | 0.1-10 |
| Volatile agent or mixture of volatile agents | 0.1-15 |
| Gelling agent | 0.01-5 |
| Polymeric film forming agent/Derivatives of acrylates copolymer | 0.5-30 |
| Preservative | 0.1-1 |
| Fragrance | 0.001-3 |
| Conditioner | 0.01-5 |
| Deionized water, alcohol or mixture thereof | QS |

EXAMPLE 11

Typical Method of Manufacture

A composition according to the present invention may be made according to the following general procedure. Although the process employs a specified formulation to exemplify the process employed, other compositions of the invention can be similarly prepared.

| Phase | Ingredient | wt. % |
| --- | --- | --- |
| A | Deionized Water (DM) | 36 |
| A | Hydroxyethylcellulose (HEC) | 0.5 |
| B | Triethanolamine (TEA) | 1 |
| B | Oleth-3-Phosphate | 0.5 |
| B | Isoceteth-20 | 0.5 |
| B | Palmitic Acid | 4 |
| C | SYNTAN EX-100 | 18 |
| C | DAITOSOL 5000SJ | 12 |
| C | Cocamidopropyl Betaine | 0.5 |
| D | WSJ24BAMP | 25 |
| D | LIQUAPAR | 0.5 |
| E | Isopentane | 1.5 |

Procedure:
Sprinkle HEC into water under medium/slow (400-600 RPM) tripleL blade mix. Allow HEC to fully disperse with no clumps
Cover and heat phase A to 75° C.
Add phase B ingredients about 3-5 minutes apart thereby allowing each to fully mix/disperse before adding the next
Mix the combined phases A and B at 75° C. for 10 minutes
Add phase C ingredients one at a time to the mixture of phases A and B allowing the batch temperature to come back up to 75° C. before adding next.
Mix the combination of phases A, B and C at 75° C. for 15 minutes
Remove heat and switch to sweep blade at 50 RPM
At about 45° C., add pigment dispersion (WSJ24BAMP) slowly under sweep. Use spatula to scrape sides of beaker and ensure thorough mix
At about 30° C., add preservative under sweep
Continue the sweeping mixing until the mixture reaches room temperature
Cool the mixture to about 2 to about 5° C. then add the volatile agent (isopentane), at about the same temperature, under high speed agitation. Charge the resultant mixture into a suitable pressure resistant container.

EXAMPLE 12

Typical Method of Manufacture

A composition according to the present invention may be made according to the following general procedure. Although the process employs a specified formulation to exemplify the process employed, other compositions of the invention can be similarly prepared.

| Phase | Ingredient | wt. % |
| --- | --- | --- |
| A | Demineralized Water (DM) | 41.8 |
| A | Hydroxyethylcellulose (HEC) | 1 |
| B | Syntan EX-100 | 18 |
| B | DAITOSOL 5000SJ | 10 |
| B | Sodium Laureth Ether Sulfate | 0.7 |
| B | Cocamidopropyl Betaine | 3 |
| C | WSJ24BAMP | 25 |
| C | LIQUAPAR | 0.5 |
| D | Isopentane | 1.5 |

Procedure:
Sprinkle HEC into water under slow (200-400 RPM) tripleL blade mix. Allow HEC to fully disperse with no clumps
Add phase B ingredients about 3-5 minutes apart thereby allowing each to fully mix/disperse before adding the next
Increase mix speed to 600 RPM. Cover and heat phases A and B to 60° C.
Continue to mix the mixture of phases A and B at 60° C. for 10 minutes
Remove heat and switch to sweep blade at 50 RPM
At 45° C., add pigment dispersion (WSJ24BAMP) slowly under sweep. Use spatula to scrape sides of beaker and ensure thorough mix
At 30° C., add preservative under sweep.
Continue the seeping mixing until the mixture reaches room temperature
Cool the mixture to about 2 to 5° C. then add the volatile agent (isopentane), at about the same temperature, under high speed agitation. Charge the resultant mixture into a suitable pressure resistant container.

EXAMPLE 13

Procedure To Determine Swelling of a Post-Expanding Composition

The functionality of compositions of the present invention may be evaluated according to the following procedure.
A pair of false eyelashes, preferably made of 100% sterilized human hair (an example is available as ARDELL FASHION LASHES #117) is mounted on the platform of a MORITEX I SCOPE USB video microscope. The scope is mounted on a ring stand so as to immobilize it. It is preferred to use a scope instrument that is equipped with a 30-magnification lens such as the MORITEX I SCOPE USB.

The subject composition is then introduced onto the eyelashes with an ordinary mascara brush in the manner mascara compositions are usually applied to eyelashes. Photos are taken before and after the composition is deposited onto the eyelashes. Furthermore, video can be shot from before the application of the composition to a point after the foaming or swelling ceases.

The mascara compositions of Examples 2 through 12 when tested in the manner described above will show a definite change in surface area. That is, it will be observed that after application of the post-application expanding composition to the eyelash, the composition will begin to swell/expand such that the radius of the composition encasing the lash appears to steadily increase for about 3 to 4 minutes. Upon completion of this 3 to 4 minute time span, the composition of the current invention will remain at this increased radial configuration. This increase in surface area is perceivable with the scope and the human eye as well. Furthermore, even at the increased radial configuration the composition will remain pliable on the eyelashes.

Although not wishing to be bound thereby the present inventor theorizes that the present invention may work in the following manner. When the composition of the present invention is applied to, for example, the eyelashes, the film forming agent component of the composition begins to cure. The composition begins to generate foam causing the film, which is at that point fairly elastic, to expand. The film then sets up and though it is sufficiently rigid to trap the foam contained within it, it remains sufficiently elastic to allow subsequent flex of the eyelash hair fibers upon which the composition is applied. The foamed material entrapped by the sufficiently elastic film acts to volumize the eyelashes.

The composition of the present invention when applied in the form of a mascara is advantageous in that much fewer brush stokes are required and thus manipulation is greatly reduced. For example, 3 to 5 brush stokes are typically required rather than the 14 or more brush stokes typically employed when mascara products of the prior art are applied to eyelashes. Additionally, unlike prior art mascara compositions, the composition of the present invention produces the desired volumizing effect without the need for further applications.

The composition of the present invention can be used for hair volumizing and, consequently, can be used on the hair of the head, eyebrows and eyelashes. As noted earlier, when used for volumizing it can be employed with or without a colorant, such as a pigment. When used on scalp hair that is white, no colorant, is required. However, when used on hair that is other than gray or white, a colorant, such as a pigment, is generally included in the composition of the present invention. Sufficient colorant or pigment should be utilized to mask the color of the entrapped foam, preferably sufficient colorant should be employed to impart to the hair fibers a predetermined desired amount of color.

The present invention also includes a method of imparting volume to the hair of the scalp, eyebrows or eyelashes comprising applying the composition of the present invention to such hair.

The post-application expanding compositions of the present invention may be packaged in many types of commercially available containers, including collapsible metal tubes and barrier-type aerosol dispensers. If an aerosol dispenser is employed, it is preferred that the post-application expanding composition be maintained in the container separate from the propellant by means of a bag, diaphragm or piston inside the container. This propellant is not to be confused with the volatile (blowing) agent that is a component of the composition. If a diaphragm or piston is employed, it can be driven by propellant or mechanical force, such as a spring.

Compositions according to the present invention may be packaged in, for example, the packaging systems described in U.S. Pat. Nos. 2,995,521; 3,541,581; 3,654,167; 4,405,489; 4,528,111; 4,651,503; 6,165,456 and US Patent Application Publication U.S. 2002/0122772 A1.

It should be understood that the foregoing description is only illustrative of some embodiments of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for imparting a volumizing effect to eyelashes comprising the step of contacting the eyelashes with a post-expanding composition comprising a film-forming agent, a surfactant, a solvent for the surfactant, and a volatile agent, wherein the film-forming agent is present in an amount effective to form a film that entraps at least a portion of foam formed by interaction of the volatile agent and the surfactant after the composition is applied to a eyelashes.

2. The composition of claim 1, wherein the composition includes about 1 to about 50% by weight of the film-forming agent, based on the total weight of the composition.

3. The composition of claim 1, wherein the composition includes about 5 to about 40% by weight of the film-forming agent, based on the total weight of the composition.

4. The composition of claim 1, wherein the composition includes about 8 to about 30% by weight of the film-forming agent, based on the total weight of the composition.

5. The composition of claim 1, wherein the composition includes about 10 to about 25% by weight of the film-forming agent, based on the total weight of the composition.

6. The composition of claim 1, wherein the film-forming agent is a polymer.

7. The composition of claim 1, wherein the film-forming agent is a copolymer.

8. The composition of claim 7, wherein the film-forming agent is selected from the group consisting of an acrylates copolymer, methacrylates copolymer, acrylamides copolymer, and mixtures thereof.

9. The composition of claim 1, wherein the composition contains a colorant.

10. The composition of claim 9, wherein the colorant is a pigment.

11. The composition of claim 10 wherein the pigment is a pigment dispersion.

12. The composition of claim 11, wherein the pigment dispersion comprises water, an iron oxide and a second film forming agent.

13. The composition of claim 1, wherein the composition contains a water-soluble viscosity increasing agent.

14. The composition of claim 13, wherein the water-soluble viscosity increasing agent is selected from the group consisting of synthetic sucrose derivatives, cellulose gums and hydrophilic colloids.

15. The composition of claim 1, wherein the composition is a gel, an emulsion or semi-solid in form.

16. The composition of claim 1, wherein the composition is a gel based on an interpolymer gel reaction product.

17. The composition of claim 16, wherein the composition contains about 0.05 to about 5% of the interpolymer gel reaction product.

18. The composition of claim 16, wherein the interpolymer gel reaction product is formed from a quaternized cationic polymer and an anionic polymer.

19. The composition of claim 1, wherein the composition contains an anionic surfactant.

20. The composition of claim 19, wherein the anionic surfactant is selected from the group consisting of water-soluble salts of $C_{10}$ to $C_{22}$ fatty acids, alkyl sulfates, alkyl ether sulfates, alkyl monoglyceryl ether sulfates, alkyl monoglyceride sulfates, alkyl monoglyceride sulfonates, alkyl sulfonates, alkylaryl sulfonates, alkyl sulfosuccinates, alkyl ether sulfosuccinates, alkyl sulfosuccinates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, alkyl ether phosphates, and mixtures thereof.

21. The composition of claim 20, wherein the water-soluble salts of $C_{10}$ to $C_{22}$ fatty acids are selected from the group consisting of sodium, potassium and triethanolanine salts of palmitic acid, stearic acid, oleic acid, myristic acid, palm and coconut oil fatty acids, and mixtures thereof.

22. The composition of claim 1, wherein the composition contains an amphoteric or zwitterionic surfactant.

23. The composition of claim 22, wherein the amphoteric or zwitterionic surfactant is selected from the group consisting of amphocarboxylates, alkyl betaines, amidoalkyl betaines, amidoalkyl sultaines, amphophosphates, phosphobetaines, pyrophosphobetaines, carboxyalkyl alkyl polyamines, alkyl amino monoacetates, alkyl amino diacetates, and mixtures thereof.

24. The composition of claim 1, wherein the composition contains a nonionic surfactant.

25. The composition of claim 24, wherein the nonionic surfactant is a polyoxyethylene derivatives of a polyol ester.

26. The composition of claim 1, wherein the volatile agent has a vapor pressure from about 0.5 Torr to about 30,000 Torr, at a temperature of about 0° to about 100° C.

27. The composition of claim 26, wherein the vapor pressure is from about 5.0 Torr to about 5,000 Torr.

28. The composition of claim 26, wherein the vapor pressure is from about 100 Torr to about 2,500 Torr.

29. The composition of claim 1, wherein the volatile agent is selected from the group consisting of n-pentane, isopentane, neopentane, n-butane, isobutane, isobutene, cyclopentane, hexane, trichlorotrifluorethane, 1,2-dichloro,1,1,2,2-tetrafluoroethane, hydrofluoroethers, and mixtures thereof.

* * * * *